United States Patent
Hatahori et al.

(10) Patent No.: US 10,317,190 B2
(45) Date of Patent: Jun. 11, 2019

(54) VIBRATION MEASUREMENT DEVICE

(71) Applicant: SHIMADZU CORPORATION, Kyoto-shi, Kyoto (JP)

(72) Inventors: Takahide Hatahori, Kyoto (JP); Yuya Nagata, Kyoto (JP); Kenji Takubo, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 15/938,591

(22) Filed: Mar. 28, 2018

(65) Prior Publication Data

US 2018/0283847 A1 Oct. 4, 2018

(30) Foreign Application Priority Data

Mar. 29, 2017 (JP) ................. 2017-064905

(51) Int. Cl.
  *G01B 9/02* (2006.01)
  *G01M 7/02* (2006.01)
  (Continued)

(52) U.S. Cl.
  CPC ..... *G01B 9/02096* (2013.01); *G01B 9/02098* (2013.01); *G01B 11/2441* (2013.01);
  (Continued)

(58) Field of Classification Search
  CPC .......... G01B 9/02096; G01B 11/2441; G01M 7/025; G01N 21/8806; G01N 21/1717;
  (Continued)

(56) References Cited

U.S. PATENT DOCUMENTS 4,567,769 A    2/1986  Barkhoudarian
4,581,939 A *  4/1986  Takahashi .......... G01N 29/2418
                                                      356/432

(Continued)

FOREIGN PATENT DOCUMENTS

CN   107462581 A   12/2017
JP   2004-101189 A  4/2004
JP   2017-219318 A  12/2017

OTHER PUBLICATIONS

Toshinori Nakajima, "Vibration Analysis by Holography", Oyo-Butsuri, 1972, pp. 560-573, vol. 41, No. 6.

(Continued)

*Primary Examiner* — Dominic J Bologna
(74) *Attorney, Agent, or Firm* — Sughrue Mion, PLLC (57) ABSTRACT

A vibration measurement device includes: a vibration-inducing section; a laser source; a scanning section for illuminating a partial area of a measurement area on an object with laser light and moving the illumination area; an illumination control section for sequentially illuminating each point within the measurement area with an illuminating duration equal to or shorter than one third of the vibration period; a displacement measurement section for measuring, for each point within the measurement area, an interfering light obtained by splitting an object light from the object into two bundles of light to measure a relative displacement in a back-and-forth direction between two closely-located points within the measurement area; and a vibration state determination section for determining the state of vibration of the entire measurement area, based on the relative displacement in the back-and-forth direction between two closely-located points at each point within the measurement area.

18 Claims, 7 Drawing Sheets

(51) Int. Cl.
*G01B 11/24* (2006.01)
*G01N 21/17* (2006.01)
*G01N 21/45* (2006.01)
*G01N 21/88* (2006.01)
*G01N 29/00* (2006.01)

(52) U.S. Cl.
CPC ........ *G01M 7/025* (2013.01); *G01N 21/8806* (2013.01); *G01N 29/00* (2013.01); *G01N 21/1717* (2013.01); *G01N 21/45* (2013.01); *G01N 2021/1706* (2013.01); *G01N 2021/8809* (2013.01); *G01N 2201/0697* (2013.01)

(58) Field of Classification Search
CPC ................... G01N 21/45; G01N 29/00; G01N 2021/1706; G01N 2021/8809; G01N 2201/0697
See application file for complete search history.

(56) References Cited

U.S. PATENT DOCUMENTS

| | | |
|---|---|---|
| 5,439,157 A | 8/1995 | Geier et al. |
| 5,546,187 A | 8/1996 | Pepper et al. |
| 6,057,927 A | 5/2000 | Lévesque et al. |
| 2003/0037616 A1* | 2/2003 | Vikhagen ........... G01B 11/2441 73/643 |
| 2003/0057972 A1* | 3/2003 | Pfaff ................... G01R 15/241 324/754.23 |
| 2003/0067609 A1* | 4/2003 | Morita ............... G01B 11/2441 356/512 |
| 2005/0023434 A1 | 2/2005 | Yacoubian |
| 2007/0157730 A1 | 7/2007 | Ochiai et al. |
| 2008/0243441 A1* | 10/2008 | Chen .................. G01B 11/2441 702/190 |
| 2009/0007678 A1 | 1/2009 | Fukutomi et al. |
| 2011/0284508 A1 | 11/2011 | Miura et al. |
| 2012/0300608 A1 | 11/2012 | Masumura |
| 2013/0329953 A1* | 12/2013 | Schreier .................. G06T 7/579 382/103 |
| 2015/0148654 A1 | 5/2015 | Whanwook et al. |
| 2016/0265900 A1 | 9/2016 | Yang et al. |
| 2017/0176393 A1 | 6/2017 | O'Donnell et al. |
| 2017/0350690 A1 | 12/2017 | Hatahori et al. |

OTHER PUBLICATIONS

Yoshiaki Kanno et al., "Measurement of Quartz Crystal Resonator's Vibration by Laser Horogaphic Interferometer", Bulletin of the Faculty of Engineering, Hokkaido University, 1982, pp. 13-20, No. 109.
Communication dated Jul. 31, 2018 from the United States Patent and Trademark Office in counterpart U.S. Appl. No. 15/611,254.
Communication dated Oct. 22, 2018 from the United States Patent and Trademark Office in counterpart U.S. Appl. No. 16/004,966.

* cited by examiner

Fig. 4A
PHASE OF VIBRATION: $\phi_0$

Fig. 4B
PHASE OF VIBRATION: $\phi_1 = \phi_0 + 2\pi/3$

Fig. 4C
PHASE OF VIBRATION: $\phi_2 = \phi_0 + 4\pi/3$

VIBRATION MEASUREMENT DEVICE

TECHNICAL FIELD

The present invention relates to a method and device for measuring a vibration on the surface of an object, such as a concrete or steel structure, for a non-contact detection and measurement of a defect on the surface or in the inside of the object, or for other related purposes.

BACKGROUND ART

In a technique for a non-contact detection and measurement of a defect on the surface or in the inside of an object, such as a concrete or steel structure, a vibration is induced in the object by means of a vibrator, and a vibration analysis is performed by optically measuring the distribution of the amplitude of the vibration on the surface of the object (for example, see Patent Literature 1). An image obtained by the vibration analysis shows a discontinuity due to a defect inside the object, thereby enabling a non-contact detection of the inner defect.

Patent Literature 1 discloses a method for examining an object having a rough surface. In this method, the entire examination area on an object to be examined is illuminated with laser light produced by expanding a laser beam using a beam expander. The laser light is scattered on the rough surface, forming a light-and-dark pattern called the "speckle" due to the mutual interference of the scattered rays of light. This speckle pattern is made to interfere with a reference laser light branched from the illuminating laser beam, and an interference image is taken with a CCD camera or similar device. Two such images are respectively taken before and after the occurrence of a displacement on the surface of the object due to an externally given elastic wave. The distribution of the displacement on the examination area is calculated from those two images. By such a technique, the measurement of the entire examination area can be performed at one time.

CITATION LIST

Patent Literature

Patent Literature 1: JP 2004-101189 A

Non Patent Literature

Non Patent Literature 1: Toshinori Nakajima, "Horogurafii Ni Yoru Shindou Kaiseki (Vibration Analysis Using Holography)", *Oyo-Buturi*, Vol. 41, No. 6 (1972), pp. 560-573

Non Patent Literature 2: Yoshiaki Kanno, et al., "Measurement of Quartz Crystal Resonator's Vibration by Laser Holographic Interferometer", *Bulletin of the Faculty of Engineering, Hokkaido University*, No. 109 (1982), pp. 13-20

SUMMARY OF INVENTION

Technical Problem

In the method described in Patent Literature 1, the speckle pattern is measured at only two points before and after excitation by the elastic wave, and only one phase state of the elastic wave can be measured. For example, if the wavelength of the elastic wave is short as compared to the size of the measurement area, there will be a region with a large amplitude of the wave and a region with a small amplitude within the measurement area. The magnitude of the displacement at a defect region changes depending on the state of the wave. Therefore, measuring only one phase state results in the defect-inspecting capability being uneven depending on the location.

The problem to be solved by the present invention is to provide a vibration measurement method and device capable of evenly examining a measurement area of an object to be examined.

Solution to Problem

To solve the aforementioned problem, the present applicant has proposed a vibration measurement method in a prior application (Japanese Unexamined Patent Application Publication No. 2017-219318). This vibration measurement method (which is hereinafter called the "prior method") includes: a process of inducing an elastic wave in an object to be examined; a process of stroboscopically illuminating a measurement area on a surface of the object; a process of collectively measuring a displacement in a back-and-forth direction of each point within the measurement area in at least three mutually different phases of the elastic wave by controlling the phase of the elastic wave and the timing of the stroboscopic illumination; and a process of detecting a defect within the measurement area, based on the displacement in the back-and-forth direction of each point within the measurement area in the at least three different phases.

In the prior method, a vibration whose time waveform is expressed by a continuous periodic function is the measurement target. During the measurement, the entire measurement area of the vibrating object is simultaneously illuminated with laser light. For the illumination, laser light with lighting duration ts is turned on synchronously with the phase of the vibration (stroboscopic illumination). Such a phase-synchronized lighting operation is repeated over a large number of periods.

The light reflected from the surface of the illuminated object ("object light") and light which is not cast onto the object ("reference light") are guided onto the same plane. The two rays of light are made to interfere with each other on this plane, and an image of this plane is taken to obtain an interference image ("reference light method"). By measuring the change in the luminance of each pixel of the interference image while changing the optical path difference of the object light and reference light, the optical phase difference between the object light and the reference light projected onto each pixel can be determined. The displacement at each point on the object can be determined from the optical phase difference. The displacement determined in this manner is a displacement observed at a phase time of the vibration when the object is stroboscopically illuminated. The displacement at a different phase time can be measured by shifting the phase-time relationship between the strobe illumination and the vibration. In the case of a vibration having a single frequency component, if the displacement is measured at three or more points in phase time, the time waveform of the original vibration can be reproduced by an approximation using the least squares method, and the amplitude and phase of the vibration can be calculated from the reproduced waveform. In the case of a vibration which is not a single-frequency vibration but additionally contains an nth-order harmonic component, the amplitude and phase of the nth-order harmonic component can be calculated by determining the displacement at 2n+1 or more points in phase time.

In such a measurement, if a displacement due to the vibration occurs within a single lighting duration ts, the obtained image will have a low level of sharpness. In order to obtain a measurement result with high sharpness, the lighting duration ts of the laser light must be sufficiently short so that the vibration can be approximately considered as standing still. However, an extreme reduction of the lighting duration ts significantly decreases the (accumulated) amount of light and lowers the SN ratio. The appropriate lighting duration ts for a desired sharpness changes depending on the magnitude of the vibration amplitude a. Therefore, it is necessary to explore an appropriate lighting duration ts for the vibration that needs to be measured. Typically, the duration is set within a range from ⅛ to ¹⁄₅₀ of the vibration period (see Non Patent Literature 1 or 2).

In a measurement using the prior method, an increase in the size of the measurement area decreases the illuminance at each point, i.e. the amount of light per unit area, and lowers the SN ratio. Taking this into account, the present inventors have improved the prior method and have conducted research on a vibration measurement method and device with which the measurement can be performed with a high level of sharpness as well as a high SN ratio without decreasing the illuminance at each point even if the target object has a large measurement area. Consequently, the present invention has been conceived.

The first vibration measurement method according to the present invention developed in light of the previously described matters includes:

a) a process of inducing a vibration in an object;

b) a process of illuminating a partial area of a measurement area on the object with laser light and moving the illumination area within the measurement area in such a manner that each point within the measurement area is illuminated with the laser light with an illuminating duration equal to or shorter than one third of the period of the vibration at a point in time synchronized with the phase of the vibration;

c) a process of measuring, for each point within the measurement area, an interfering light produced by an interference between a reference light split from the laser light before the laser light is cast onto the illumination area and an object light reflected from the point illuminated with the laser light;

d) a process of measuring, for each point within the measurement area, a displacement in a back-and-forth direction of the point by changing an optical path difference of the reference light and the object light by a distance depending on the wavelength of the laser light; and e) a process of determining the state of vibration of the entire measurement area, based on the displacement in the back-and-forth direction at each point within the measurement area, where the displacement is measured at three or more different points in time within one period of the vibration, and the points in time are each synchronized with the phase of the vibration.

In the first vibration measurement method according to the present invention, while a vibration is being induced in an object (process a)), a partial area (illumination area) of a measurement area on the object is illuminated with laser light, and this illumination area is sequentially moved within the measurement area (process b)). In other words, the measurement area is scanned with the laser light. The duration of the laser illumination at each point is equal to or shorter than one third of the period of the vibration. The point in time of the illumination is synchronized with the phase of the vibration. The illumination phase time (the phase position within one period of the vibration) does not always need to be the same at all illumination points within the measurement area; the illumination phase time may vary from point to point.

Such a scan of the measurement area is performed at three or more different illumination phase times within one period of the vibration for each point within the measurement area (process e)). It is for this reason that the duration of the laser illumination at each point is made to be equal to or shorter than one third of the period of the vibration. In the vibration measurement method according to the present invention, a portion of the measurement area is illuminated with laser light at one time, and this illumination area is moved within the measurement area. Therefore, for example, if the scanning frequency is the same as the vibration frequency, it is possible to make the illuminating duration at each point within the measurement area equal to or shorter than one third of the period of the vibration while using a laser source whose lighting duration is equal to or longer than one third of the period of the vibration. A laser source which generates continuous light can also be used in the case where an area which is equal to or smaller than one third of the measurement area is illuminated with the laser light and this illumination area is moved within the measurement area.

While the measurement area is being scanned with such a laser light illumination, an interfering light produced by an interference between the reference light split from the laser light before the laser light is cast onto the illumination area and the object light reflected by the illuminated object is measured (process c)). Furthermore, the displacement of each point in the back-and-forth direction is measured by changing the optical path difference of the reference light and the object light by an amount depending on the wavelength of the laser light (process d)). This is a conventionally known displacement measurement method employing a reference light method. An absolute magnitude of the displacement can be measured by this method.

Based on the measured displacements in the back-and-forth direction at each point within the measurement area, the state of the vibration over the entire measurement area can be determined (process e)).

If a defect is present within the measurement area of the object, the displacement in the back-and-forth direction of the points within the area discontinuously changes at the site of the defect. Accordingly, the defect in the measurement area of the object can be detected by examining the state of the vibration within the measurement area by using the present invention.

Figure 1:
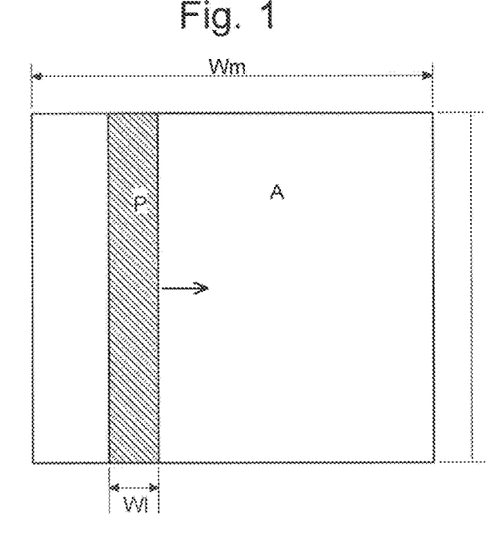
FIG. 1 is a diagram illustrating the operation of scanning a measurement area A with a laser illumination area P in a vibration measurement device according to the present invention.

This method is hereinafter specifically described with reference to FIG. 1. In this example, an area P (illumination area) of width Wl, which is a partial area within the entire measurement area A, is illuminated with laser light. This illumination area P is one-dimensionally moved (scanning operation). Initially, the case where the vibration frequency fv is equal to the scanning frequency fs is considered. In this case, for example, if the width Wl of the illumination area P and the length Wm of the measurement area A are chosen so that Wl/Wm=1/8, the illuminating duration Tl at each point within the measurement area A will be one eighth of the vibration period Tv. The light source can be continuously lit during this scan. Therefore, the luminance can be eight times as high as the level achieved by the conventional method in which the entire measurement area A is simultaneously illuminated with a pulsed laser beam for a duration which is equal to one eighth of the vibration period Tv.

By using such a line scan illumination, an optical interference measurement is performed in a similar manner to a conventional technique to measure the displacement due to the vibration. The displacement is measured at three or more points in phase time of the vibration by shifting the phase relationship between the scan and vibration. The phase and amplitude of the vibration at each point within the measurement area is determined from the measured displacements. The phase time of the original vibration of the vibrator is hereinafter called the "vibrator phase time" and used as the reference. In the present method, the vibrator phase time at which the illumination is initiated (which is called the "initial phase time") varies from point to point. However, it is possible to compute the vibration state of all points for the same vibrator phase time by correcting the phase of the measured vibration using the initial phase time at each point.

Next, the case where the vibration frequency fv is different from the scanning frequency fs is considered. In this case, the scanning frequency fs should be equal to 1/N of the vibration frequency fv (where N is an integer equal to or greater than two). This is useful in the case where the used scan mechanism has an upper limit of the scanning frequency that is not sufficiently high for the frequency of the vibration that needs to be measured. For example, if the ratio of the vibration frequency to the scanning frequency is fv/fs=5, the condition of Tl/Tv=1/8 can be achieved by setting Wl/Wm=1/40. Thus, in the case of the line scan, the illuminating duration at each point can be controlled by appropriately setting the ratio between the length of the illumination area and that of the measurement area.

The measurement area may be two-dimensionally scanned with a small illumination area, instead of being one-dimensionally scanned with a linear illumination area as in the previously described example.

The second vibration measurement method according to the present invention developed in light of the previously described matters is a method employing a speckle-shearing method for obtaining an interfering light, including:

a) a process of inducing a vibration in an object;

b) a process of illuminating a partial area of a measurement area on the object with laser light and moving the illumination area within the measurement area in such a manner that each point within the measurement area is illuminated with the laser light with an illuminating duration equal to or shorter than one third of the period of the vibration at a point in time synchronized with the phase of the vibration;

c) a process of measuring, for each point within the measurement area, an interfering light obtained by splitting an object light reflected from the object into two bundles of light and making the two bundles of light interfere with each other with a slight angular difference, to measure a relative displacement in a back-and-forth direction between two closely-located points within the measurement area; and d) a process of determining the state of vibration of the entire measurement area, based on the relative displacement in the back-and-forth direction between two closely-located points at each point within the measurement area, where the displacement is measured at three or more different points in time within one period of the vibration, and the points in time are each synchronized with the phase of the vibration.

In any of the two methods, the displacement measurement is performed at least three points in time synchronized with the phase of the vibration. It is further preferable to use 2n+1 or more points in time synchronized with the phase (where n is a natural number equal to or greater than two) so that an nth-order component (nth-order harmonic component) of the elastic wave induced in the object can be detected from the displacement in the back-and-forth direction of each point within the measurement area. If a defect is present in the object, the discontinuous change which occurs at the site of the defect as mentioned earlier contains a significant amount of higher-order component. The smaller the defect is, the higher the proportion of such a higher-order component is. Accordingly, the accuracy of the defect detection can be improved by detecting a higher-order component.

A vibration measurement device according to the present invention for carrying out the first vibration measurement method (reference light method) includes:

a) a vibration-inducing section for inducing a vibration in an object;

b) a laser source;

c) a scanning section for illuminating a partial area of a measurement area on the surface of the object with light from the laser source, and for moving the illumination area within the measurement area;

d) an illumination control section for controlling the vibration-inducing section, the laser source and the scanning section so as to sequentially illuminate each point within the measurement area with the laser light with an illuminating duration equal to or shorter than one third of the period of the vibration at a point in time synchronized with the phase of the vibration;

e) an interfering light measurement section for measuring, at each point within the measurement area, an interfering light produced by an interference between a reference light split from the laser light before the laser light is cast onto the illumination area and an object light reflected from the point illuminated with the laser light;

f) a displacement measurement section for measuring, for each point within the measurement area, a displacement in a back-and-forth direction of the point by changing an optical path difference of the reference light and the object light by a distance depending on the wavelength of the laser light; and g) a vibration state determination section for determining the state of vibration of the entire measurement area, based on the displacement in the back-and-forth direction at each point within the measurement area, where the displacement is measured at three or more different points in time within one period of the vibration, and the points in time are each synchronized with the phase of the vibration.

A vibration measurement device according to the present invention for carrying out the second vibration measurement method (speckle-shearing method) includes:

a) a vibration-inducing section for inducing a vibration in an object;

b) a laser source;

c) a scanning section for illuminating a partial area of a measurement area on the surface of the object with light from the laser source, and for moving the illumination area within the measurement area;

d) an illumination control section for controlling the vibration-inducing section, the laser source and the scanning section so as to sequentially illuminate each point within the measurement area with the laser light with an illuminating duration equal to or shorter than one third of the period of the vibration at a point in time synchronized with the phase of the vibration;

e) a displacement measurement section for measuring, for each point within the measurement area, an interfering light obtained by splitting an object light reflected from the object into two bundles of light and making the two bundles of light interfere with each other with a slight angular difference, to measure a relative displacement in a back-and-forth direction between two closely-located points within the measurement area; and f) a vibration state determination section for determining the state of vibration of the entire measurement area, based on the relative displacement in the back-and-forth direction between two closely-located points at each point within the measurement area, where the displacement is measured at three or more different points in time within one period of the vibration, and the points in time are each synchronized with the phase of the vibration.

Advantageous Effects of the Invention

In the vibration measurement method and device according to the present invention, the measurement is performed while the laser illumination area is sequentially moved within the measurement area. Therefore, the measurement can be performed with a high SN ratio without decreasing the illuminance at each point even if the target object has a large measurement area. Furthermore, since the illuminating duration at each point is shortened, a high-sharpness measurement with little blurring due to the vibration can be achieved.

DESCRIPTION OF EMBODIMENTS

An embodiment of the vibration measurement method and device according to the present invention is hereinafter described using FIGS. 1-9. The method and device in the present embodiment are used as a defect inspection method and device for a non-contact detection and measurement of a defect on the surface or in the inside of an object. The method and device can also be used for various purposes other than the defect inspection, such as a non-destructive examination of the inner structure of a structural object.

Figure 2:
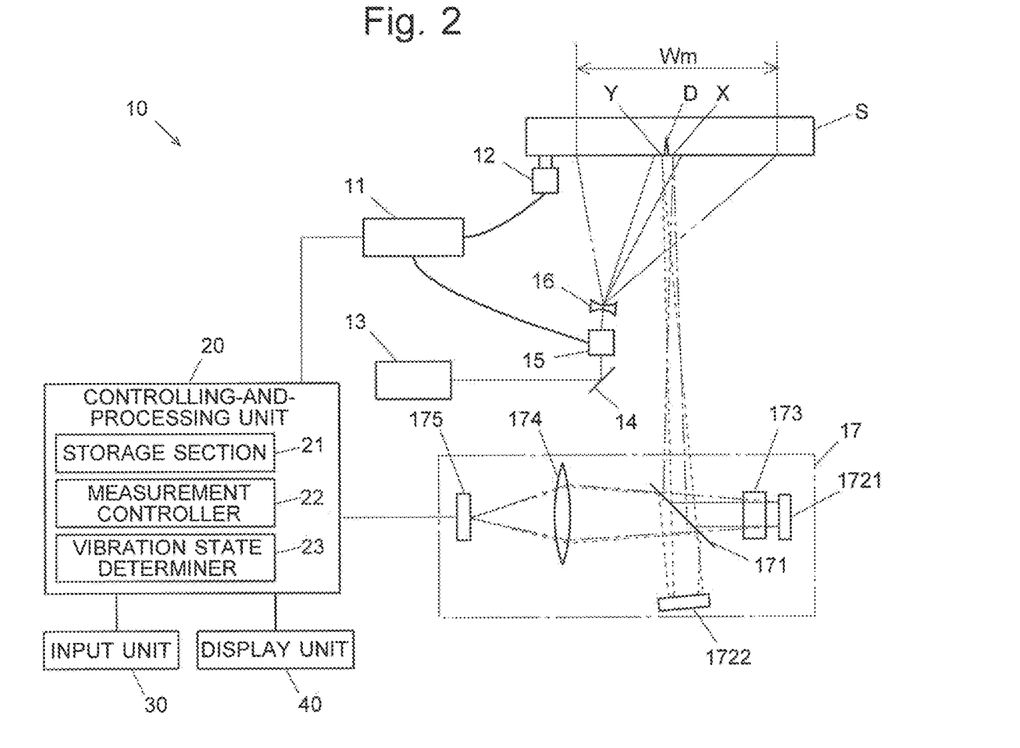
FIG. 2 is a schematic configuration diagram of a defect inspection device as one embodiment of the vibration measurement device according to the present invention.

FIG. 2 is a schematic configuration diagram of the defect inspection device 10 in the present embodiment. The defect inspection device 10 includes a signal generator 11, vibrator 12, laser source 13, mirror 14, deflector 15, illuminating light lens 16, speckle-shearing interferometer 17 as well as a controlling-and-processing unit 20.

The signal generator 11, which is connected to the vibrator 12 by a cable, generates an AC electric signal and sends it to the vibrator 12. When in use, the vibrator 12 is held in contact with an object S to be examined. The vibrator 12 receives the AC electric signal from the signal generator 11, converts it into a mechanical vibration, and gives the vibration to the object S. An elastic-wave vibration is thereby induced in the object S. The signal generator 11 and the vibrator 12 correspond to the vibration-inducing section mentioned earlier.

The signal generator 11 is also connected to the deflector 15 by a cable different from the one connected to the vibrator 12. The deflector 15 receives light which is emitted from the laser source 13 synchronously with the period of the AC electric signal, and makes the light move within a measurement area on the object S. The signal generator 11 and the deflector 15 correspond to the scanning section mentioned earlier.

The laser source 13 is a light source for continuously generating laser light. The light from the laser source 13 is reflected by the mirror 14 and enters the deflector 15. After being deflected, the light is shaped by the illuminating light lens 16 and cast onto the measurement area A (see FIG. 1) on the object S. The illuminating light lens 16 has the function of expanding the light from the laser source 13 to the size of an illumination area P which scans the measurement area on the surface of the object S. For example, it is a concave lens having different radii of curvature in two orthogonal directions. The measurement area A and illumination area P in the present embodiment both have rectangular shapes. The illumination area P has the same length as the measurement area A in one direction (vertical direction in FIG. 1), while the length W1 of the illumination area P in the other direction (horizontal direction in FIG. 1) is one eighth of the length Wm of the measurement area A. Accordingly, the area of the illumination area P is one eighth of the measurement area A.

The speckle-shearing interferometer 17 corresponds to the displacement measurement section mentioned earlier. It splits an object light reflected from the object S into two bundles of light and makes them interfere with each other with a slight angular difference. The speckle-shearing interferometer 17 includes a beam splitter 171, first reflector 1721, second reflector 1722, phase shifter 173, condensing lens 174, and image sensor 175. The beam splitter 171 is a half mirror arranged in a manner to receive the illuminating light (object light) reflected by the measurement area A on the surface of the object S. The first reflector 1721 is located on an optical path of the object light reflected by the beam splitter 171. The second reflector 1722 is located on an optical path of the object light passing through the beam splitter 171. The phase shifter 173, which is located between the beam splitter 171 and the first reflector 1721, changes (shifts) the phase of the light which passes through the phase shifter 173. The image sensor 175 is located on an optical path of two bundles of object light; one bundle of light is initially reflected by the beam splitter 171 and subsequently by the first reflector 1721, to eventually pass through the beam splitter 171 into the aforementioned optical path, while the other bundle of light initially passes through the beam splitter 171 and is subsequently reflected by the second reflector 1722, to be eventually reflected by the beam splitter 171 into the same optical path. The condensing lens 174 is located between the beam splitter 171 and the image sensor 175.

The first reflector 1721 is arranged so that its reflecting surface is at an angle of 45° to that of the beam splitter 171, whereas the second reflector 1722 is arranged so that its reflecting surface is slightly tilted from 45° to the reflecting surface of the beam splitter 171. Such an arrangement of the first and second reflectors 1721 and 1722 produces two rays of object light falling onto the same position on the image sensor 175 and interfering with each other, with one ray of light being reflected by point X on the surface of the object S and the first reflector 1721 (as indicated by long dashed short dashed lines in FIG. 2) and the ray of light being reflected by point Y slightly displaced from point X on the object surface and the second reflector 1722 (as indicated by dashed lines in FIG. 2). The image sensor 175 has a large number of detector elements arranged in a two-dimensional form. Each detector element detects light originating from a different point (point X mentioned earlier) on the surface of the object S and falling onto the image sensor 175 via the first reflector 1721 and the phase shifter 173. Similarly, as for the point Y, each detector element detects light originating from a different one of the large number of points and falling onto the image sensor 175 via the second reflector 1722. The visual field of the image sensor 175 is adjusted to capture the entire measurement area A.

The controlling-and-processing unit 20 includes a storage section 21 as well as a measurement controller 22 and a vibration state determiner 23 as its functional block. The measurement controller 22 controls the signal generator 11. The vibration state determiner 23 performs data-processing operations based on the detection signals obtained from the detector elements of the image sensor 175. The data storage section 21 stores the detection signals obtained from the detector elements of the image sensor 175 and the data obtained through the data-processing by the vibration state determiner 23. The controlling-and-processing unit 20 is actually a personal computer. The aforementioned functional blocks are embodied by a CPU executing a vibration measurement software program in the same computer. An input unit 30 including a keyboard and mouse as well as a display unit 40 are connected to the controlling-and-processing unit 20.

Figure 3:
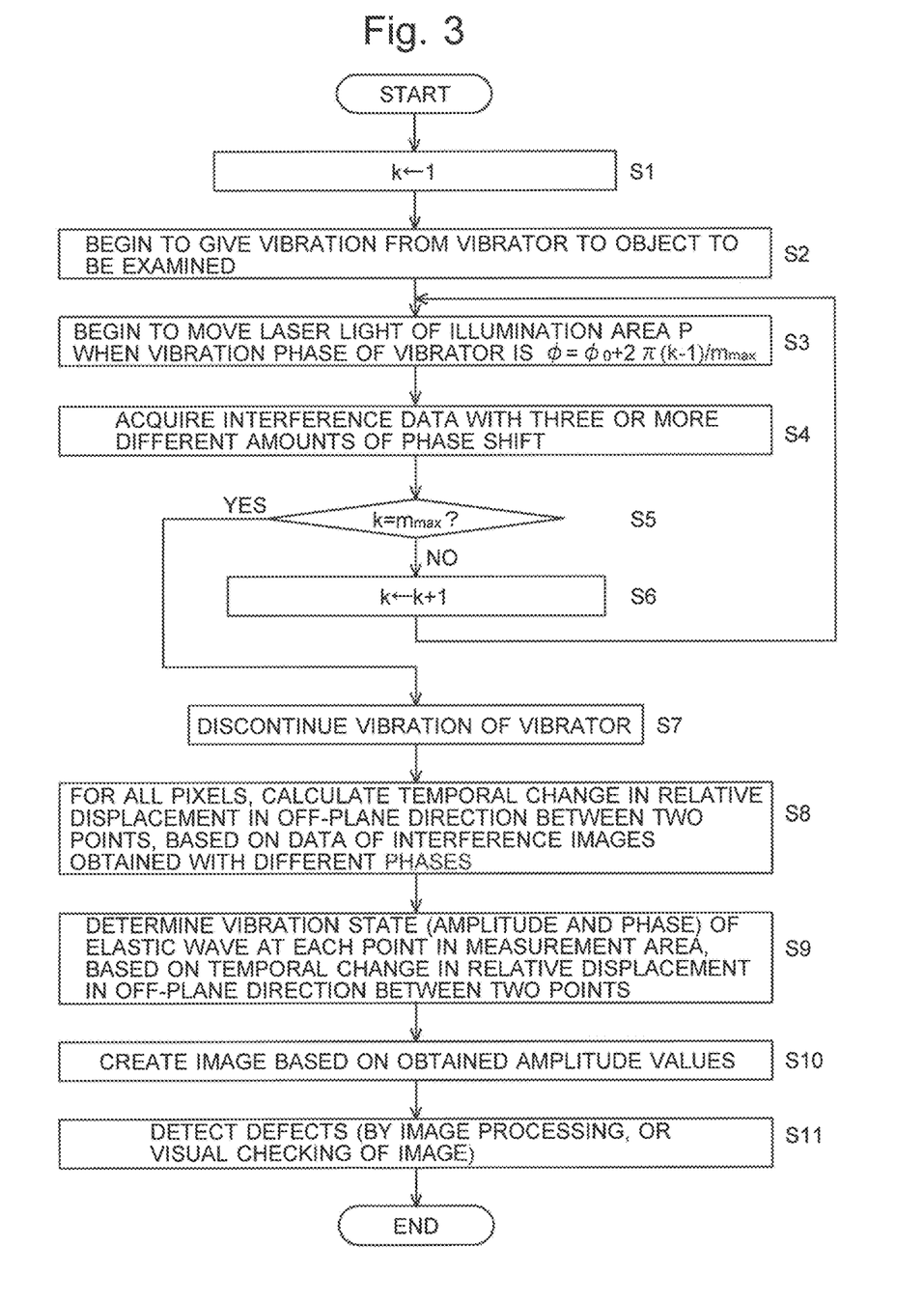
FIG. 3 is a flowchart of a defect inspection method as one embodiment of the vibration measurement method according to the present invention.
Figure 4A:
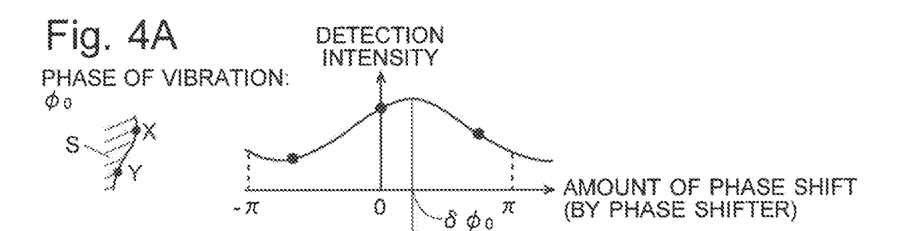
FIGS. 4A-4C are graphs for explaining the principle of the defect inspection method in the present embodiment.

An operation of the defect inspection device 10 according to the present embodiment is hereinafter described using the flowchart in FIG. 3 and the graph in FIG. 4. In the present embodiment, the measurement area A on the object S is scanned from one end (left side in FIG. 1) to the other end (right side in FIG. 1) by the laser illumination area P at scanning frequency fs. The scanning frequency fs is the same as the vibration frequency fv of the mechanical vibration given from the vibrator 12 and propagated through the object S, i.e. fs=fv. Since the width Wl of the illumination area P is one eighth of the length Wm of the measurement area A, the illuminating duration at each point in the measurement area A in the present embodiment is one eighth of the period of the mechanical vibration. It should be noted that the two frequencies do not always need to be the same, as will be explained later. While the laser light is moving across the measurement area A, the shutter of the image sensor 175 is maintained in the open state to accumulate the intensity of the light falling onto each detector element of the image sensor 175.

In the present embodiment, the measurement is performed at $m_{max} \geq 3$ points in time (three or more different points in vibrator phase time) corresponding to different phases of the vibration of the vibrator 12. The "phase of the vibration of the vibrator 12" is the phase of the AC electric signal sent from the signal generator 11 to the vibrator 12. It corresponds to the phase of the elastic wave induced in the object S at the point where the vibrator 12 is in contact with the object S. The measurement performed each time is hereinafter called the "measurement at the kth vibrator phase time", using a numerical value k (which is a natural number from 1 to $m_{max}$). The following description initially deals with the case of $m_{max}=3$ as the simplest example and explains all steps. After that, a case with a greater value of $m_{max}$ will be described.

Initially, the value of k is set to 1 (Step S1). An AC electric signal is sent from the signal generator 11 to the vibrator 12 to begin the operation of giving a vibration from the vibrator 12 to the object S (Step S2). Consequently, an elastic wave is induced in the object S.

Subsequently, the signal generator 11 transmits a pulse signal to the deflector 15 at a point in time corresponding to a phase of the vibration of the vibrator 12 expressed as $\varphi_0 + 2\pi(k-1)/m_{max}$ (i.e. at a vibrator phase time of $\varphi_0 + 2\pi(k-1)/m_{max}$), where $\varphi_0$ is a predetermined initial value (e.g. $\varphi_0=0$). At this stage, since k=1, the phase of the vibration of the vibrator 12 at the point of transmission of the pulse signal is $\varphi_0$. Upon receiving the pulse signal, the deflector 15 initiates the operation of making the laser light of the illumination area P move from one end of the measurement area A. As described earlier, this laser light is expanded by the illuminating light lens 16 to illuminate an area corresponding to one eighth of the measurement area A on the object S (Step S3).

The illuminating light is reflected on the surface of the object S. The object light from this surface hits the beam splitter 171 in the speckle-shearing interferometer 17. A portion of this incident object light is reflected by the beam splitter 171. After passing through the phase shifter 173, this object light is reflected by the first reflector 1721 and once more passes through the phase shifter 173. A portion of this light passes through the beam splitter 171 and falls onto the image sensor 175. Meanwhile, the remaining portion of the incident object light mentioned earlier passes through the beam splitter 171. After being reflected by the second reflector 1722, a portion of this object light is reflected by the beam splitter 171 and falls onto the image sensor 175. As described earlier, each detector element on the image sensor 175 detects light reflected at one of a large number of points on the surface of the object S. The image sensor 175 also accumulates the intensity of the incident light while the laser light is moving across the measurement area A. As a result, a speckle image of the entire measurement area A is obtained. It should be noted that the intensity signals at the points forming the obtained speckle image are respectively obtained at different vibrator phase times. That is to say, the speckle image reflects the intensities of light obtained at various points in the vibrator phase time, which has a value of $\varphi_0=0$ at one end of the measurement area A where the laser-light movement is initiated and changes to a value corresponding to one period at the other end where the movement is completed. Thus, the vibrator phase time at which the illumination is initiated (which is hereinafter called the "initial phase time") differs from point to point in the speckle image. However, it is possible to compute the vibration state at all points for the same vibrator phase time by correcting the phase of the measured vibration using the initial phase time at each point.

After the scanning of the measurement area A with the illumination area P is continued for a predetermined period of time, the phase shifter 173 is moved by a predetermined distance of Δd to change (shift) the phase of the object light passing through the phase shifter 173 (i.e. the object light from point X), and the previously described measurement is once more similarly performed. This time, the phase difference between the object light from point X and the one from point Y is different from the previous measurement. Subsequently, the phase shifter 173 is once more moved by a predetermined distance of Δd (i.e. to a distance of 2×Δd from the initial position) to further change (shift) the phase of the object light passing through the phase shifter 173 (i.e. the object light from point X), and the previously described measurement is once more similarly performed. In this manner, the intensities of the interfering light with three different amounts of phase shift (as indicated by the black dots in FIG. 4A) are obtained for each point forming the measurement area A. Based on the intensities at those three points, a graph as shown in FIG. 4A can be created, which shows the intensity of the interfering light detected by a detector element of the image sensor 175 with respect to the amount of phase shift by the phase shifter 173 when the phase of the vibration of the vibrator 12 is $\varphi_0$ (Step S4). Although FIGS. 4A-4C each show a continuous curve representing the detection intensity which sinusoidally changes with the amount of phase shift, actually observed data are discrete data. Therefore, the continuous sinusoidal waveform should be reproduced from the observed data by an appropriate method, such as the least squares method. Accordingly, it is necessary to detect the intensity with at least three different amounts of phase shift, as in the present embodiment. Measuring the intensity of the interfering light with four or more different amounts of phase shift is also possible, although the measurement in the present embodiment is performed with three different amounts of phase shift.

Subsequently, whether or not the value of k has reached $m_{max}$ is determined (Step S5). At this stage, since the value is k=1 and has not reached $m_{max}$ (which is 3 in this example), the determination result in Step S5 is "NO". When "NO", the operation proceeds to Step S6 and the value of k is increased by 1 to k=2. (The operation which is performed when the determination result in Step S5 is "YES" will be described later.)

Next, the operation returns to Step S3. The signal generator 11 transmits a pulse signal to the deflector 15 at every point in time where the phase of the vibration of the vibrator 12 is $\varphi_0+2\pi(k-1)/m_{max}$ with k=2, i.e. $\varphi_0+2\pi/3 \equiv \varphi_1$ (vibrator phase time $\varphi_1$). Upon receiving the pulse signal, the deflector 15 initiates the operation of making the laser light move across the measurement area A on the object S. Each detector element of the image sensor 175 detects the intensity of the interfering light formed by the object light reflected at point X and transmitted through the phase shifter 173, etc., and the object light reflected at point Y. As in the previously described measurement, the intensity of the light falling onto each detector element of the image sensor 175 during the scan with the laser light is accumulated and stored in the storage section 21. As described earlier, such a measurement of the intensity of the interfering light for each point forming the measurement area A is performed with three different amounts of phase shift, and a graph is created which shows the intensity of the interfering light detected by a detector element of the image sensor 175 with respect to the amount of phase shift by the phase shifter 173 at a vibrator phase time of $\varphi_1$ (Step S4).

Figure 4B:
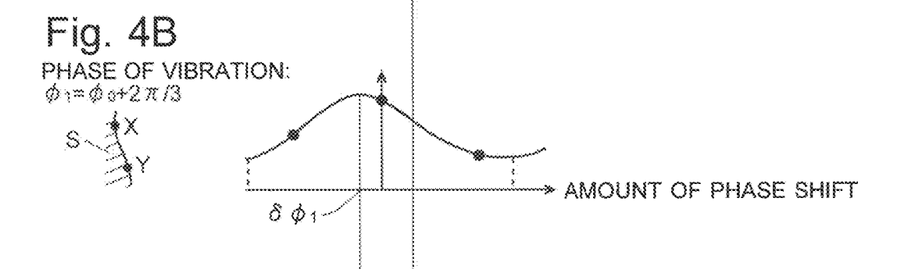
Figure 4C:
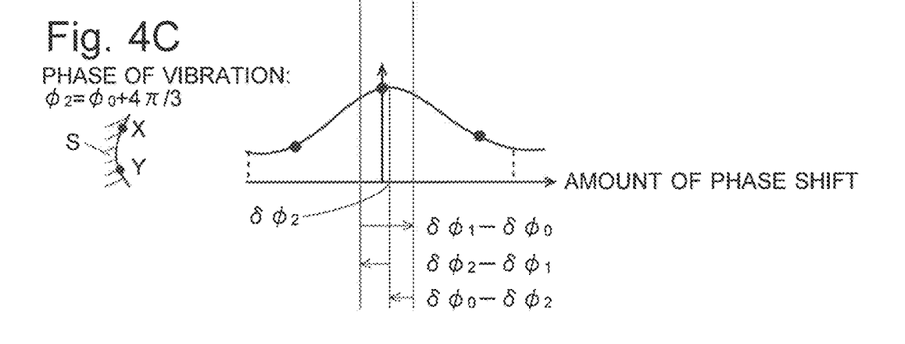

FIG. 4B graphically shows the intensity of the interfering light detected by a detector element of the image sensor 175 with respect to the amount of phase shift by the phase shifter 173 at a vibrator phase time of $\varphi_1$. A comparison of FIGS. 4B and 4A demonstrates that the peak position of the intensity of the interfering light in FIG. 4B is displaced from the peak position in FIG. 4A by $\delta\varphi_0-\delta\varphi_1$. This displacement indicates that the phase difference between the light from point X and the light from point Y has changed due to the change in the phase of the vibration of the vibrator 12 in the detecting process. This change in the phase difference of the light reflects a change in the relative displacement of points X and Y in the off-plane direction.

When the measurement for k=2 has been completed, $m_{max}$ (=3) is not yet reached ("NO" in Step S5). Accordingly, the value of k is increased by 1 to k=3 in Step S6. Subsequently, the operation returns to Step S3. The deflector 15 scans the measurement area A on the object S with the laser light at every point in time where the phase of the vibration of the vibrator 12 is $\varphi_0+2\pi(k-1)/m_{max}$ with k=3, i.e. $\varphi_0+4\pi/3 \equiv \varphi_2$ (vibrator phase time $\varphi_2$). The intensity of the interfering light is measured by each detector element of the image sensor 175. Once again, as in the previous measurements, the intensity of the interfering light for each point forming the measurement area A is measured with three different amounts of phase shift, and a graph is created which shows the intensity of the interfering light detected by a detector element of the image sensor 175 with respect to the amount of phase shift by the phase shifter 173 at a vibrator phase time of $\varphi_2$ (FIG. 4C; Step S4).

Now, since the value of k has reached $m_{max}$=3 ("YES" in Step S5), the operation subsequently proceeds to Step S7. In Step S7, the transmission of the AC electric signal from the signal generator 11 to the vibrator 12 is discontinued. The vibration of the vibrator 12 is thereby stopped. The sequence of operations described thus far are performed under the command of the measurement controller 22. The measurement in the present embodiment is performed in such a manner that the interference data are obtained with three different amounts of phase shift while the initial phase time is fixed. It is also possible to perform the measurement in such a manner that the initial phase time is sequentially changed while the amount of phase shift is fixed. That is to say, it is possible to perform Step S4 (acquisition of interference data with three or more different amounts of phase shift) after the determination result in Step S5 has been "YES", and to return to Step S3 after resetting the value of k to 1.

Next, in Steps S8 and S9, the vibration state determiner 23 computes the vibration state (amplitude and phase) of the elastic wave at each point in the measurement area as follows:

Initially, the measurement signals at each detector element of the image sensor 175 (the signals constituting the speckle image) are corrected with the initial phase time at each point of the speckle image so that all measurement signals correspond to the same vibrator phase time. Subsequently, for each detector element of the image sensor 175, the amount of phase shift at which the detector element yields the highest output during the operation of changing the amount of phase shift by the phase shifter 173 is determined as the output-maximizing phase-shift amount $\delta\varphi_0$, $\delta\varphi_1$ or $\delta\varphi_2$ for each of the phases of the vibration $\varphi_0$, $\varphi_1$ and $\varphi_2$, respectively (see the graphs in FIGS. 4A-4C). Then, the difference in the output-maximizing phase-shift amount is calculated for each different combination of the phases of the vibration, i.e. $\delta\varphi_1-\delta\varphi_0$, $\delta\varphi_2-\delta\varphi_1$ and $\delta\varphi_0-\delta\varphi_2$ (Step S8). These three differences in the output-maximizing phase-shift amount show three different relative displacements of the points X and Y in the off-plane direction by two pieces of data obtained with different phases of the vibration of the vibrator 12 (i.e. with different vibrator phase times). Based on the three different relative displacements, the values of the following three parameters can be obtained: the amplitude of the vibration, phase of the vibration, and central value (DC component) of the vibration at each point in the measurement area A (Step S9).

Based on the amplitude value of the vibration at each point obtained in this manner, an image of the object S is created (Step S10). For example, the difference in the amplitude of the vibration can be represented by a difference in the brightness level in the image by assigning a higher level of luminance to a pixel corresponding to a measurement point with a greater amplitude.

The image created in the previously described manner is subsequently processed by a commonly known image-processing technique, to detect defect D on the surface of the object S (Step S11). For example, a portion where the luminance of the pixel suddenly changes with a positional change on the image may be detected as a defect. The detection of the defect may be performed by a visual check by an inspector in place of the image processing. Detecting a defect in the measurement area without creating an image is also possible, e.g. by detecting a point of discontinuity. With the completion of the process in Step S11, the operation of the defect inspection device 10 and the entire process of the defect inspection method in the present embodiment is completed.

The present invention is not limited to the previous embodiment.

Although $m_{max}=3$ in the previous embodiment, $m_{max}$ may be changed to a value expressed as 2n+1 (where n is a natural number equal to or greater than 2) so as to detect the nth-order component (nth-order harmonic component) of the elastic wave induced in the object S. That is to say, since 2n+1 or more relative displacements of the points X and Y in the off-plane direction are obtained, the values of the following 2n+1 parameters can be obtained: the amplitude of the fundamental harmonic, the phase of the fundamental harmonic, the amplitude of the second-order harmonic, the phase of the second-order harmonic, . . . , the amplitude of the nth-order harmonic, the phase of the nth-order harmonic, and the DC component of the elastic wave.

In the previous embodiment, the signal generator 11 and the vibrator 12 as well as the signal generator 11 and the deflector 15 are connected by cables (wired connections). They may be connected by wireless connections. It is particularly preferable to wirelessly connect the signal generator 11 and the vibrator 12. The use of a wireless connection between the signal generator 11 and the vibrator 12 allows the vibrator 12 to be held in contact with the object S without using a long cable even when the components of the defect inspection device 10 are located far from the object S. For example, such a wireless configuration is beneficial in the case of examining a large-scale object S, such as a bridge or other forms of infrastructure.

The vibrator 12 in the previous embodiment is made to be in contact with the surface of the object S when in use. In place of such a vibrator, a high-power speaker or similar device placed without being in contact with the surface of the object S may be used.

Windows and/or various optical filters for some purposes, such as protecting optical components or improving the SN ratio of the device, may be arranged on the optical path of the light reflected from the object S and falling onto the image sensor in the previous embodiment. Examples of the various optical filters include polarizers, wave plates, band-pass filters, short pass filters, long pass filters and so on.

Although the condensing lens 174 in the previous embodiment is arranged between the beam splitter 171 and the image sensor 175, the arrangement is not limited to this example. The condensing lens 174 may be composed of a plurality of lenses or lens groups. For example, the condensing lens 174 may be composed of a first lens group and second lens group, with the first lens group arranged between the object S and the beam splitter 171, and the second lens group arranged between the beam splitter 171 and the image sensor 175. The first lens group may be configured as a part that can be detached without requiring the dismantling of the housing of the speckle-shearing interferometer 17. This configuration allows the angle of view to be easily changed by replacing the first lens group with another lens group having a different focal length. For example, the angle of view can be adjusted to set an appropriate size of the measurement area according to the distance between the object S and the speckle-shearing interferometer 17 so that the defect inspection can be performed for objects S at various positions. Examples of the lenses available as the first lens group include telephoto lenses, wide angle lenses, macro lenses, zoom lenses, and so on.

Figure 5:
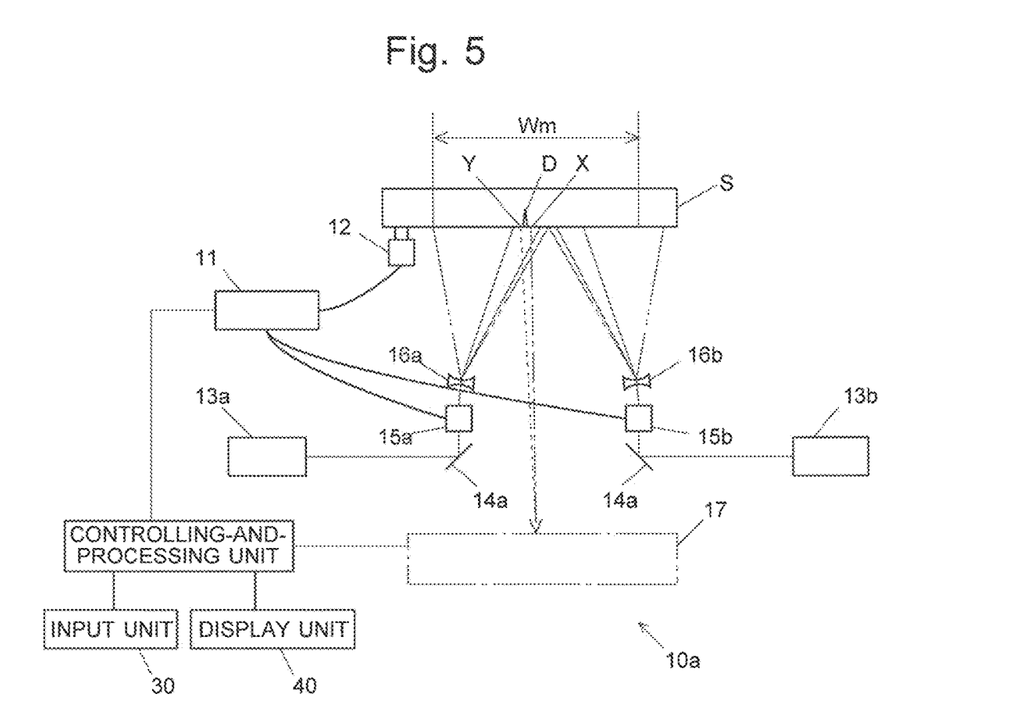
FIG. 5 is a schematic configuration diagram of a modified example of the defect inspection device in the present embodiment.
Figure 6:
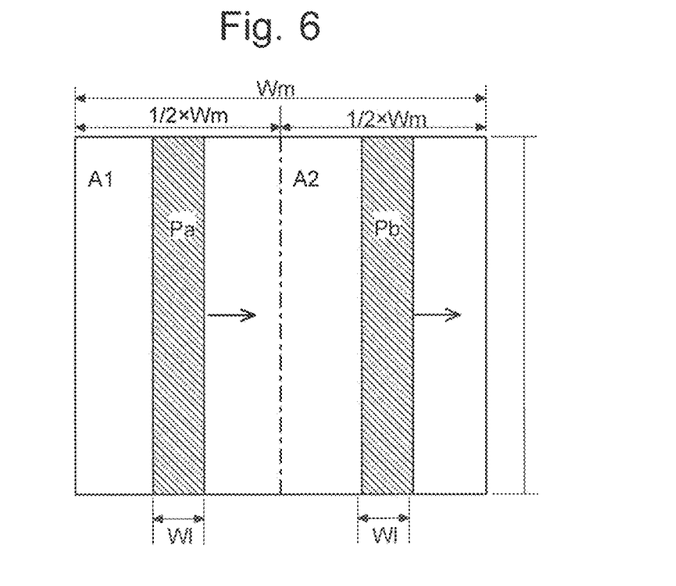
FIG. 6 is a diagram illustrating the operation of scanning a measurement area A with laser light in the modified example of the defect inspection device.

Additionally, in the previous embodiment, a single light-source unit (laser source 13, mirror 14, deflector 15 and illuminating light lens 16) is used to scan the measurement area A. A configuration with two or more light-source units is also possible. For example, as shown in FIG. 5 (where the inner configuration of the speckle-shearing interferometer 17 is omitted), two light-source units may be used, one of which includes a laser source 13a, mirror 14a, deflector 15a and illuminating light lens 16a, while the other unit includes a laser source 13b, mirror 14b, deflector 15b and illuminating light lens 16b. In this case, the measurement area A can be scanned with two laser beams, whereby the length of time for the measurement can be reduced to one half.

In the previous embodiment, the interference image is obtained by a speckle-shearing method. Alternatively, a reference light method may be employed to obtain the interference image. In that case, the laser beam is split into two beams. One beam is cast onto the object S. The thereby reflected beam and the other beam (which is not cast onto the object S) are guided onto the same plane and made to interfere with each other.

Figure 7:
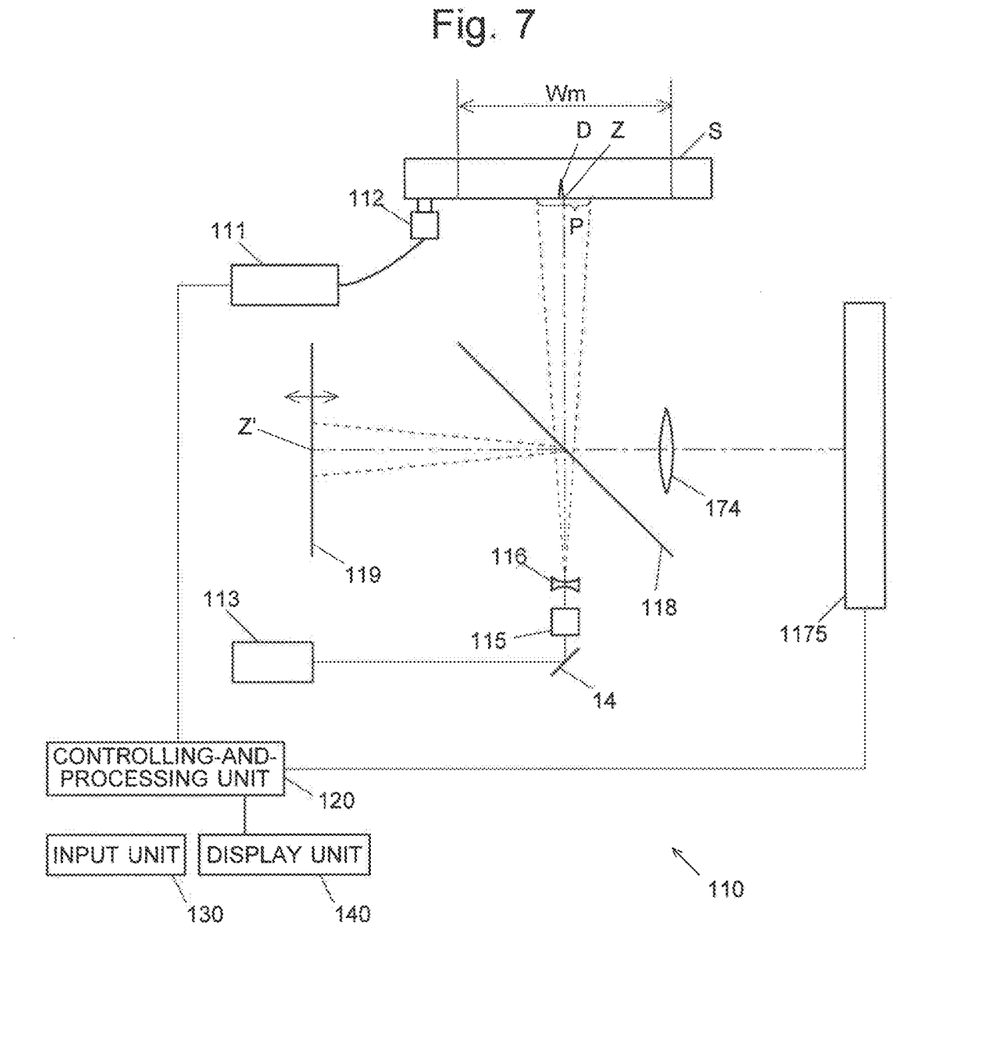
FIG. 7 is a schematic configuration diagram of a defect inspection device as another embodiment of the vibration measurement device according to the present invention.

FIG. 7 schematically shows the configuration of a vibration measurement device employing the reference light method. The same components as used in FIG. 2 are denoted by numerals having the same last two or three digits as used in FIG. 2. Descriptions of such components will be omitted.

In the present vibration measurement device, the light which has passed through the deflector 115 and the illuminating light lens 116 is split into two beams by the beam splitter 118. One beam (transmitted light) is cast onto the object S to be examined. The light cast onto and reflected by the illumination area P on the object S is reflected by the beam splitter 118 and enters the image sensor 1175. The other beam (reflected light), which has been reflected by the beam splitter 118 after passing through the illuminating light lens 116, is reflected by a movable mirror 119. Then, the light passes through the beam splitter 118 and enters the image sensor 1175. A ray of light reflected from point Z in the illumination area P on the object S interferes with another ray of light which is reflected from point Z' on the movable mirror 119 without being cast onto the object S. The interfering light passes through the condensing lens 174 and falls onto a point on the detection surface of the image sensor 1175. Thus, an interference image of the illumination area P is created on the detection surface of the image sensor 1175. The procedure for scanning the measurement area A on the object S with the laser light is the same as in the previous embodiment. The procedure for changing the amount of phase shift by using the movable mirror 119 is commonly known. Accordingly, descriptions of those procedures will be omitted.

Figure 8:
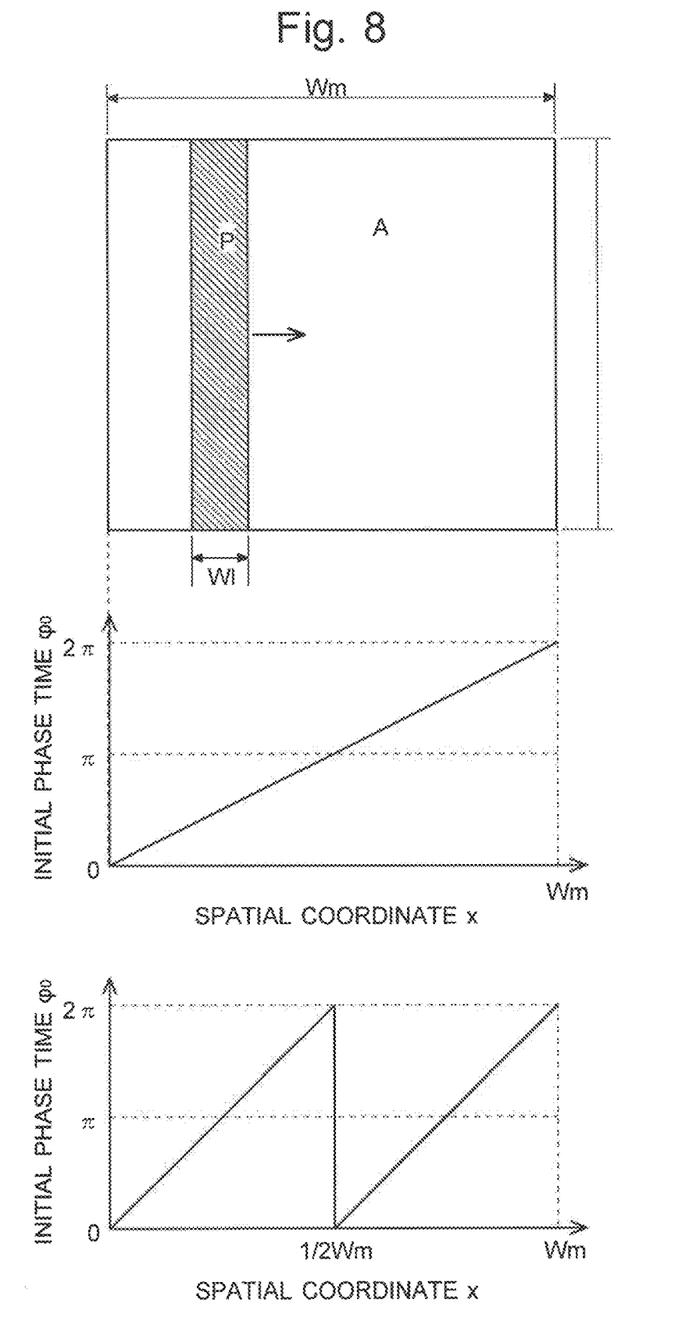
FIG. 8 is a diagram illustrating the scanning frequency at which the measurement area A is scanned.

In each of the previously described embodiments, the scanning frequency fs of the laser light is set to be equal to the vibration frequency fv of the mechanical vibration which is given from the vibrator 12 and propagated through the object S, as shown in the middle section of FIG. 8. The two frequencies do not always need to be equal to each other. For example, as shown in the lower section of FIG. 8, the scanning frequency fs of the laser light may be one half of the vibration frequency fv. In this case, two periods of mechanical vibration are propagated through the measurement area A while this area is scanned with the laser light one time. Such a configuration may be adopted if there is an upper limit of the scanning frequency fs of the laser light due to the construction of the deflector 15 and it is difficult to make fs equal to the frequency fv of the mechanical vibration. In such a case, the following equation holds true for the lighting duration Tl of the laser light at each point within the measurement area A and the vibration period Tv:

$$\frac{T_l}{T_v} = \frac{W_l \cdot f_v}{W_m \cdot f_s} \qquad (1)$$

where Wm is the length of the measurement area in the scanning direction, Wl is the length of the illumination area in the scanning direction, fv is the vibration frequency, and fs is the scanning frequency.

Figure 9:
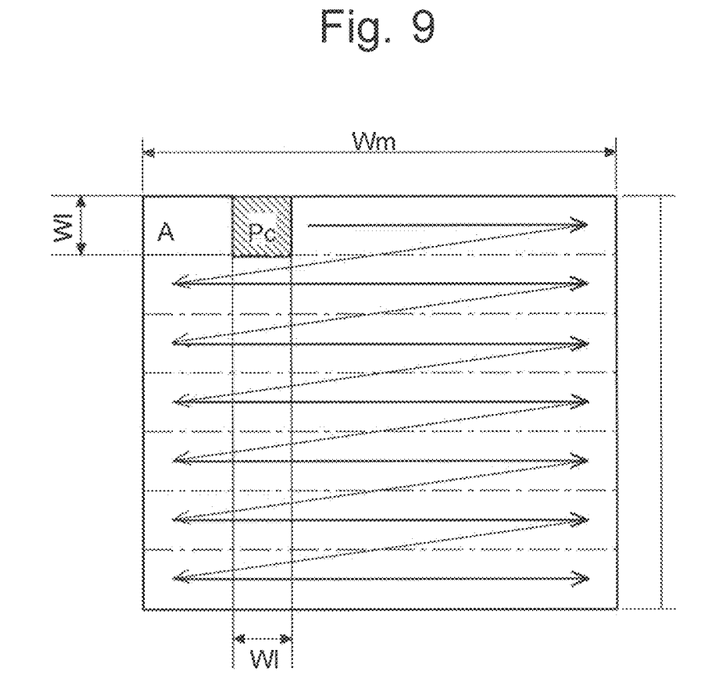
FIG. 9 is a diagram illustrating an example in which the measurement area A is two-dimensionally scanned with laser light.

In any of the previously described embodiments, the illumination area P of the laser light is one eighth of the measurement area A, and the length of time to illuminate each point in the measurement area A with the laser light is one eighth of the vibration period. However, the illuminating duration at each point may have any length equal to or shorter than one third of the vibration period. Using a shorter illuminating duration improves the sharpness of the interference image, while causing a decrease in the amount of illuminating light. With these factors considered, the illuminating duration should be appropriately determined, preferably within a range from one eighth to one fiftieth of the vibration frequency. Furthermore, although the measurement area is one-dimensionally scanned with a linear illumination area in any of the previous embodiments, a two-dimensional scan is also possible. FIG. 9 shows an example, in which the measurement area A is two-dimensionally scanned with a small square illumination area Pc.

REFERENCE SIGNS LIST 10, 10a, 110 . . . Defect Inspection Device
   11, 111 . . . Signal Generator
   12, 112 . . . Vibrator
   13, 13a, 13b, 113 . . . Laser Source
   14, 14a, 14b, 114 . . . Mirror
   15, 15a, 15b, 115 . . . Deflector
   16, 16a, 16b . . . Illuminating Light Lens
   17 . . . Speckle-Shearing Interferometer
   171 . . . Beam Splitter
   1721 . . . First Reflector
   1722 . . . Second Reflector
   173 . . . Phase Shifter
   174 . . . Condensing Lens
   175, 1175 . . . Image Sensor
   118 . . . Beam Splitter
   119 . . . Movable Mirror
20 . . . Controlling-and-Processing Unit
   21 . . . Storage Section
   22 . . . Measurement Controller
   23 . . . Vibration State Determiner
30 . . . Input Unit
40 . . . Display Unit
D . . . Defect
S . . . Object to Be Examined

The invention claimed is:

1. A vibration measurement device, comprising:
  a) a vibration-inducing section for inducing a vibration in an object;
  b) a laser source;
  c) a scanning section for illuminating a partial area of a measurement area on a surface of the object with light from the laser source, and for moving the illumination area within the measurement area;
  d) an illumination control section for controlling the vibration-inducing section, the laser source and the scanning section so as to sequentially illuminate each point within the measurement area with the laser light with an illuminating duration equal to or shorter than one third of a period of the vibration at a point in time synchronized with a phase of the vibration;
  e) a displacement measurement section for measuring, for each point within the measurement area, an interfering light obtained by splitting an object light reflected from the object into two bundles of light and making the two bundles of light interfere with each other with a slight angular difference, to measure a relative displacement in a back-and-forth direction between two closely-located points within the measurement area; and
  f) a vibration state determination section for determining a state of vibration of the entire measurement area, based on the relative displacement in the back-and-forth direction between two closely-located points at each point within the measurement area, where the displacement is measured at three or more different points in time within one period of the vibration, and the points in time are each synchronized with the phase of the vibration.

2. The vibration measurement device according to claim 1, wherein an area of the illumination area is within arrange from one fiftieth to one eighth of an area of the measurement area.

3. The vibration measurement device according to claim 1, wherein a scanning frequency of the illumination area moved by the scanning section is 1/m of a vibration frequency of the vibration, where m is a natural number.

4. The vibration measurement device according to claim 1, wherein the number of the points in time synchronized with the phase is equal to or greater than 2n+1, where n is a natural number, and an nth-order harmonic component of the vibration is detected from the displacement in the back-and-forth direction of each point within the measurement area.

5. The vibration measurement device according to claim 1, wherein a lighting duration of the laser source is equal to or longer than one third of the period of the vibration.

6. The vibration measurement device according to claim 1, wherein:
the laser source includes a plurality of laser-source units;
each of the laser-source units illuminates a different partial area of the measurement area on the surface of the object; and
the scanning section moves each illumination area within the measurement area.

7. A defect inspection device, comprising the vibration measurement device according to claim 1.

8. A vibration measurement device, comprising:
a) a vibration-inducing section for inducing a vibration in an object;
b) a laser source;
c) a scanning section for illuminating a partial area of a measurement area on a surface of the object with light from the laser source, and for moving the illumination area within the measurement area;
d) an illumination control section for controlling the vibration-inducing section, the laser source and the scanning section so as to sequentially illuminate each point within the measurement area with the laser light with an illuminating duration equal to or shorter than one third of the period of the vibration at a point in time synchronized with a phase of the vibration;
e) an interfering light measurement section for measuring, at each point within the measurement area, an interfering light produced by an interference between a reference light split from the laser light before the laser light is cast onto the illumination area and an object light reflected from the point illuminated with the laser light;
f) a displacement measurement section for measuring, for each point within the measurement area, a displacement in a back-and-forth direction of the point by changing an optical path difference of the reference light and the object light by a distance depending on a wavelength of the laser light; and
g) a vibration state determination section for determining a state of vibration of the entire measurement area, based on the displacement in the back-and-forth direction at each point within the measurement area, where the displacement is measured at three or more different points in time within one period of the vibration, and the points in time are each synchronized with the phase of the vibration.

9. The vibration measurement device according to claim 8, wherein an area of the illumination area is within arrange from one fiftieth to one eighth of an area of the measurement area.

10. The vibration measurement device according to claim 8, wherein a scanning frequency of the illumination area moved by the scanning section is 1/m of a vibration frequency of the vibration, where m is a natural number.

11. The vibration measurement device according to claim 8, wherein the number of the points in time synchronized with the phase is equal to or greater than 2n+1, where n is a natural number, and an nth-order harmonic component of the vibration is detected from the displacement in the back-and-forth direction of each point within the measurement area.

12. The vibration measurement device according to claim 8, wherein a lighting duration of the laser source is equal to or longer than one third of the period of the vibration.

13. The vibration measurement device according to claim 8, wherein:
the laser source includes a plurality of laser-source units;
each of the laser-source units illuminates a different partial area of the measurement area on the surface of the object; and
the scanning section moves each illumination area within the measurement area.

14. A defect inspection device, comprising the vibration measurement device according to claim 8.

15. A vibration measurement method, comprising:
a) a process of inducing a vibration in an object;
b) a process of illuminating a partial area of a measurement area on the object with laser light and moving the illumination area within the measurement area in such a manner that each point within the measurement area is illuminated with the laser light with an illuminating duration equal to or shorter than one third of a period of the vibration at a point in time synchronized with a phase of the vibration;
c) a process of measuring, for each point within the measurement area, an interfering light obtained by splitting an object light reflected from the object into two bundles of light and making the two bundles of light interfere with each other with a slight angular difference, to measure a relative displacement in a back-and-forth direction between two closely-located points within the measurement area; and
d) a process of determining a state of vibration of the entire measurement area, based on the relative displacement in the back-and-forth direction between two closely-located points at each point within the measurement area, where the displacement is measured at three or more different points in time within one period of the vibration, and the points in time are each synchronized with the phase of the vibration.

16. A defect inspection method, comprising the processes described in claim 15.

17. A vibration measurement method, comprising:
a) a process of inducing a vibration in an object;
b) a process of illuminating a partial area of a measurement area on the object with laser light and moving the illumination area within the measurement area in such a manner that each point within the measurement area is illuminated with the laser light with an illuminating duration equal to or shorter than one third of a period of the vibration at a point in time synchronized with a phase of the vibration;
c) a process of measuring, for each point within the measurement area, an interfering light produced by an interference between a reference light split from the laser light before the laser light is cast onto the illumination area and an object light reflected from the point illuminated with the laser light;
d) a process of measuring, for each point within the measurement area, a displacement in a back-and-forth direction of the point by changing an optical path difference of the reference light and the object light by a distance depending on a wavelength of the laser light; and
e) a process of determining a state of vibration of the entire measurement area, based on the displacement in the back-and-forth direction at each point within the measurement area, where the displacement is measured at three or more different points in time within one period of the vibration, and the points in time are each synchronized with the phase of the vibration.

18. A defect inspection method, comprising the processes described in claim 17.

* * * * *